United States Patent [19]

Murphy

[11] Patent Number: 5,474,891
[45] Date of Patent: Dec. 12, 1995

[54] PLASMA-BASED PLATELET CONCENTRATE PREPARATIONS WITH ADDITIVE

[75] Inventor: Scott Murphy, Ardmore, Pa.

[73] Assignee: Thomas Jefferson University, Philadelphia, Pa.

[21] Appl. No.: 262,045

[22] Filed: Jun. 16, 1994

Related U.S. Application Data

[63] Continuation-in-part of Ser. No. 43,574, Apr. 7, 1993, Pat. No. 5,344,752, which is a continuation-in-part of Ser. No. 784,695, Oct. 30, 1991, Pat. No. 5,234,808.

[51] Int. Cl.$^6$ ..................................................... A01N 1/02
[52] U.S. Cl. .................................................. 435/2; 424/532
[58] Field of Search ................................. 435/2; 424/532

[56] References Cited

U.S. PATENT DOCUMENTS

| Re. 32,874 | 2/1989 | Rock et al. | 424/101 |
|---|---|---|---|
| 4,447,415 | 5/1984 | Rock et al. | 424/101 |
| 4,529,705 | 7/1985 | Larsen | 436/17 |
| 4,695,460 | 9/1987 | Holme | 424/101 |
| 4,769,318 | 9/1988 | Hamasaki et al. | 435/2 |
| 4,828,976 | 5/1989 | Murphy | 435/2 |
| 4,831,117 | 5/1989 | Uckun | 530/387 |
| 4,880,786 | 11/1989 | Sasakawa et al. | 514/53 |
| 4,992,363 | 2/1991 | Murphy | 435/2 |
| 4,994,367 | 2/1991 | Bode et al. | 435/2 |

OTHER PUBLICATIONS

Cesar, Diminno, Alam, Silver and Murphy in "Plasma Free Fatty Acid Metabolism During Storage of Platelet Concentrates for Transfusion", *Transfusion*, 27(5):434–437 (1987).
Guppy et al., *Vox Sanguinis*, 59:146–152 (1990).
Heaton et al., *British Journal of Hematology*, 75:400–407 (1990).
Kilkson, Holme and Murphy in "Platelet Metabolism During Storage of Platelet Concentrates at 22° C." *Blood*, 64(2):406–414.
Mollison, P. L., *Blood Transfusion in Clinical Medicine*, 7th Edition, Blackwell, 1983.
Murphy et al. in "Improved Storage of Platelets for Transfusion in a New Container", *Blood* 60(1):194–200 Jul., (1982).
Murphy in "The Preparation and Storage of Platelets for Transfusion", Mammon, Barnhart, Lusher and Walsh, PJD Publications, Ltd., Westbury, New York (1980).
Murphy in "Platelet Transfusion", *Progress in Hemostasis and Thrombosis*, vol. III, Edited by Theodore Spaet, Grune and Stratton, Inc. (1976).
Murphy et al. in "Platelets Storage at 22° C.: Role of Gas Transport Across Plastic Containers in Maintenance of Viability", *Blood* 46(2):209–218 (1975).
Murphy in "Platelet Storage for Transfusion", *Seminars in Hematology*, 23(3):165–177, (1985).
Simon, Nelson, Carmen and Murphy in "Extension of Platelet Concentrate Storage", *Transfusion*, 23:207–212, (1983).
Fijnheer, et al., In vitro Evaluation of Buffy–Coat–Derived Platelet Concentrates Stored in a Synthetic Medium, *Vox Sang.*, 60:16–22, (1991).
Adams, et al., Survival and Recovery of Human Platelets Stored for Five Days in a Non–Plasma Medium, *Blood*, 67:672–675, (1986).
Huang E. M. et al, Thrombosis Research 36:1–8 (1984).

*Primary Examiner*—Marian C. Knode
*Assistant Examiner*—S. Saucier
*Attorney, Agent, or Firm*—Woodcock Washburn Kurtz Mackiewicz & Norris

[57] ABSTRACT

The present invention provides a composition and method for improving the storage of platelets and optimizing the viability of stored platelets. The present invention allows platelets to be stored in plasma for extended periods, without the addition of buffer, by adding storage extension additives, which include acetate, pyruvate, acetoacetate, β-hydroxybutyrate, acetone, α-ketoglutarate, succinate, fumarate, malate, oxaloacetate, $C_{3-8}$ fatty acid anions, triose phosphates and mixtures thereof, to a platelet concentrate.

20 Claims, 10 Drawing Sheets

PLASMA-BASED PLATELET CONCENTRATE PREPARATIONS WITH ADDITIVE

GOVERNMENT SUPPORT

Portions of this work were supported by NIH Grant HL20818-15 from the National Institute of Health. The U.S. government may have certain rights in this invention. This application is a continuation-in-part of U.S. Ser. No. 043,574 filed Apr. 7, 1993, now U.S. Pat. No. 5,344,752, which is a continuation-in-part of U.S. Ser. No. 784,695 filed Oct. 30, 1991, now U.S. Pat. No. 5,234,808.

BACKGROUND OF THE INVENTION

The present invention relates to a composition and method to improve the storage of platelets prior to transfusion into a patient. Platelets are obtained as a by-product from whole blood donations and from plateletpheresis procedures. Typically, they are stored at 22°±2° C. in their own plasma within a plastic container whose walls are permeable to atmospheric gases. The plasma associated with these platelets normally contains all the= ingredients of normal plasma plus ingredients in the primary anticoagulant which result in a dextrose concentration five times the physiologic concentration. The dextrose is added to the primary anticoagulant for the benefit of red cells which require it during storage, and dextrose is generally accepted to be required for platelet storage as well. In routine blood banking practice, thee primary anticoagulant which is utilized is citrate-phosphate-dextrose (CPD), from Mollison, P. L., *Blood Transfusion in Clinical Medicine*, 7th Edition, Blackwell, 1983.

Donations of a unit of blood (63 ml of CPD mixed with 450 ml of whole blood) are processed by centrifugation into three fractions: red cells, plasma, and platelets. The volume of packed red cells from a unit of blood is approximately 180 ml, with a remaining volume of plasma and anticoagulant of about 333 ml. As used in the remainder of this application, the term plasma includes any anticoagulant which has been added thereto at the time of blood collection. The red cells are typically suspended in approximately 45 ml of plasma. Platelets are suspended in approximately 50 ml of plasma. This platelet containing product is typically referred to as a "platelet concentrate" (PC). The remaining 238 ml of plasma is frozen as fresh plasma. New techniques for preparing platelets for transfusion include platelet pheresis and the "buffy coat technique". During platelet pheresis, a single donor provides about five units of platelets by allowing the blood to be withdrawn and processed by a pheresis machine which separates the platelets for storage and redirects plasma, and optionally also the red cells, back to the donor. The "buffy coat technique" allows for the pooling of the platelets from several donors, usually about 4–6 donors, with the subsequent storage of the platelets in a storage medium that is either a plasma-based medium or a synthetic-based medium.

A great deal is known about human platelet cells. General papers describing techniques, materials and methods for storage of platelets are described by Murphy et al. in "Improved Storage of Platelets for Transfusion in a New Container", *Blood*, 60(1):194–200 (July, 1982); by Murphy in *"The Preparation and Storage of Platelets for Transfusion"*, Mammon, Barnhart, Lusher and Walsh, PJD Publications, Ltd., Westbury, New York (]980);by Murphy in "Platelet Transfusion", *Progress in Hemostasis and Thrombosis*, Vol. III, Edited by Theodore Spaet, Grune and Stratton, Inc. (1976); by Murphy et al. in "Platelet Storage at 22° C.: Role of Gas Transport Across Plastic Containers in Maintenance of viability", Blood, 46(2) 209–218 (1975); by Kilkson, Holme and Murphy in "Platelet Metabolism During Storage of Platelet Concentrates at 22° C.", *Blood*, 64 (2) 406–414 (1984); by Murphy in "Platelet Storage for Transfusion", *Seminars in Hematology*, 22(3) 165–177 (1985); by Simon, Nelson, Carmen, and Murphy in "Extension of Platelet Concentrate Storage", *Transfusion*, 23:207–212 (1983); by Cesar, Diminno, Alam, Silver and Murphy in "Plasma Tree Fatty Acid Metabolism During Storage of Platelet Concentrates for Transfusion", *Transfusion*, 27(5):434–437 (1987); each of which publications is hereby incorporated by reference and is more fully set forth herein.

There exists a considerable body of prior art concerning storage of platelets. Prior work has shown that the duration of platelet storage is limited by the continuing production of lactic acid from dextrose by the platelets. Although this provides energy for the platelets, the lactic acid acidifies the medium, which acidity eventually destroys the platelets. It has also been shown that platelets consume oxygen during storage for energy production, the end product of which process is a gas, $CO_2$, which unlike lactic acid, can leave the platelet concentrate through the plastic walls of the container in which it is normally stored. The production of $CO_2$ does not acidify the storage medium for the platelets. In addition to the glycolysis of dextrose, fatty acids and amino acids typically present in the plasma may be used as substrates for oxidative metabolism of stored platelet cells.

Most platelet storage media contain glucose. In U.S. Pat. No. 4,695,460 (Holme), a synthetic platelet storage media is disclosed containing 3.0–7.5 grams of dextrose, 3.0–6.0 grams of sodium citrate, and 2.0–4.2 grams of sodium bicarbonate. U.S. Pat. No. 4,447,415 (Rock) discloses a number of platelet storage solutions. It has been appreciated that platelet storage in a medium essentially free of glucose could be advantageous. For example, in U.S. Pat. No. 4,828,976, Murphy discloses a glucose free media for storing blood platelets. To store platelets for periods in excess of 5 days, it is taught that the storage media should be essentially free of glucose. It is also disclosed that it is the presence of glucose that leads to the generation of lactic acid which adversely affects platelet viability.

The rapid loss of platelet function during storage presents a significant problem in blood banking. One approach for diminishing or delaying the loss of platelet function during storage has been the development of plasma-free storage media. For example, U.S. Pat. No. 4,695,460 (Holme) and U.S. Pat. No. 4,447,414 (Rock et al.).

Another approach has focused on the biochemistry of platelet activation and means to regulate platelet activation, which results in platelet lysis and death. U.S. Pat. No. 4,994,367 (Bode et al.) discloses a blood platelet preparation comprising blood platelets, an adenylate cyclase stimulator (Prostaglandin El), a phosphodiesterase inhibitor (Theophylline), a thrombin inhibitor(N-(2-naphthylsulfonylglycyl)-D,L-amidinophenylalaninpiperidide), and a plasmin inhibitor (Aprotinin). A plasma-free platelet storage medium comprising dextrose, sodium citrate, sodium bicarbonate, and a platelet activation inhibitor (adenylate cyclase stimulator) is also disclosed. A process for preparing a plasma-free platelet preparation by producing platelet-rich plasma (PRP) from whole blood, adding a platelet activation inhibitor (adenylate cyclase stimulator), centrifuging the PRP to deposit the platelets on the bottom of the centrifuge container, removing the platelet-free plasma supernatant, and adding a plasma-free liquid platelet storage medium is also provided.

The adenylate cyclase stimulator is included to increase the production of adenosine 3',5'-cyclic phosphate (cAMP) in the blood platelets. The phosphodiesterase inhibitor is included to reduce the degradation of cAMP in the blood platelets. The thrombin inhibitor is included to reduce the stimulation of the blood platelets. The plasmin inhibitor is included to reduce the degradation of cell surface proteins on the blood platelets.

Heaton et al., *British Journal of Hematology*, 75:400–407 (1990) disclose an ionically balanced electrolyte solution with citrate, glucose and bicarbonate which was shown to provide good platelet viability with storage for up to 7 days When adenine was added to this solution, it also allowed for satisfactory preservation of red cells for extended periods.

A major problem of platelet storage in synthetic media is the potential for phi fall resulting from the lactate end product of glycolytic energy metabolism. The approach taken here is to add bicarbonate to buffer the acid load generated by a glucose-containing medium. In vivo studies demonstrated improved post-transfusion viability with platelets stored in this medium as compared to CPD-plasma.

Guppy et al., *Vox Sanguinis*, 59:146–152 (1990) studied the metabolism of platelets in vitro. It was found that glucose is never oxidized to any significant extent and is always converted to lactate, regardless of oxygen availability. Preliminary storage experiments using plasma-free media showed that an acetate-containing buffered salt solution provided excellent storage conditions and that a medium without any exogenous fuel is better than one containing glucose. Thus, it is concluded that a platelet storage medium should contain minimal amounts of glucose, and an oxidizable fuel in order to supplement the endogenous one. The identity of this fuel is not known; however, it is shown not to be glucose or glycogen. It is concluded that platelets can use acetate and when present, this fuel completely replaces the endogenous fuel. The data suggest that acetate, short chain fatty acids or amino acids metabolizable through the TCA cycle should provide ATP efficiently at low molarities without producing toxic end-products.

Notwithstanding the considerable work conducted in this area, a need still exists for means to improve the storage of platelets in a viable condition.

SUMMARY OF THE INVENTION

The present invention provides a composition and method to improve the storage of platelets in plasma. In plasma, a limiting factor for long term storage is that lactic acid production exceeds the bicarbonate buffering capacity leading to lethal pH fall at day 10–14 of storage. The present invention allows platelets to be stored in plasma for a longer period of time prior to the occurrence of pH fall, due to lactic acid production. Therefore, this invention would be useful to prolong the interval during which viable platelets can be stored in plasma.

The present invention provides a human blood, plasma-based platelet concentrate preparation for the storage of platelets. The preparation contains platelets suspended or dispersed in a solution of plasma, and the anticoagulant for the plasma as mentioned previously, and an added amount of an additive for extending the storage of the platelets. The additives include acetate, acetoacetate, betahydroxybutyrate, acetone, alpha-ketoglutarate, succinate, fumarate, malate, oxaloacetate, $C_{3-8}$ fatty acid anions, triose phosphates, pyruvate, and mixtures thereof. The invention also provides methods for storing platelets in a solution of plasma, and the anticoagulant for the plasma, with the incorporation of the additives.

Accordingly, one embodiment of the present invention provides for the addition of acetate to a platelet concentrate. Addition of acetate results in acetate being oxidized by the platelets resulting in bicarbonate formation. Thus, storage can be extended due to the better preservation of pH. As a result, the invention improves platelet transfusion therapy.

A further object of the present invention is the use of acetate to optimize platelet storage.

This and further objects of the present invention will become apparent from the following more detailed description

DETAILED DESCRIPTION OF THE INVENTION

Figure 1:
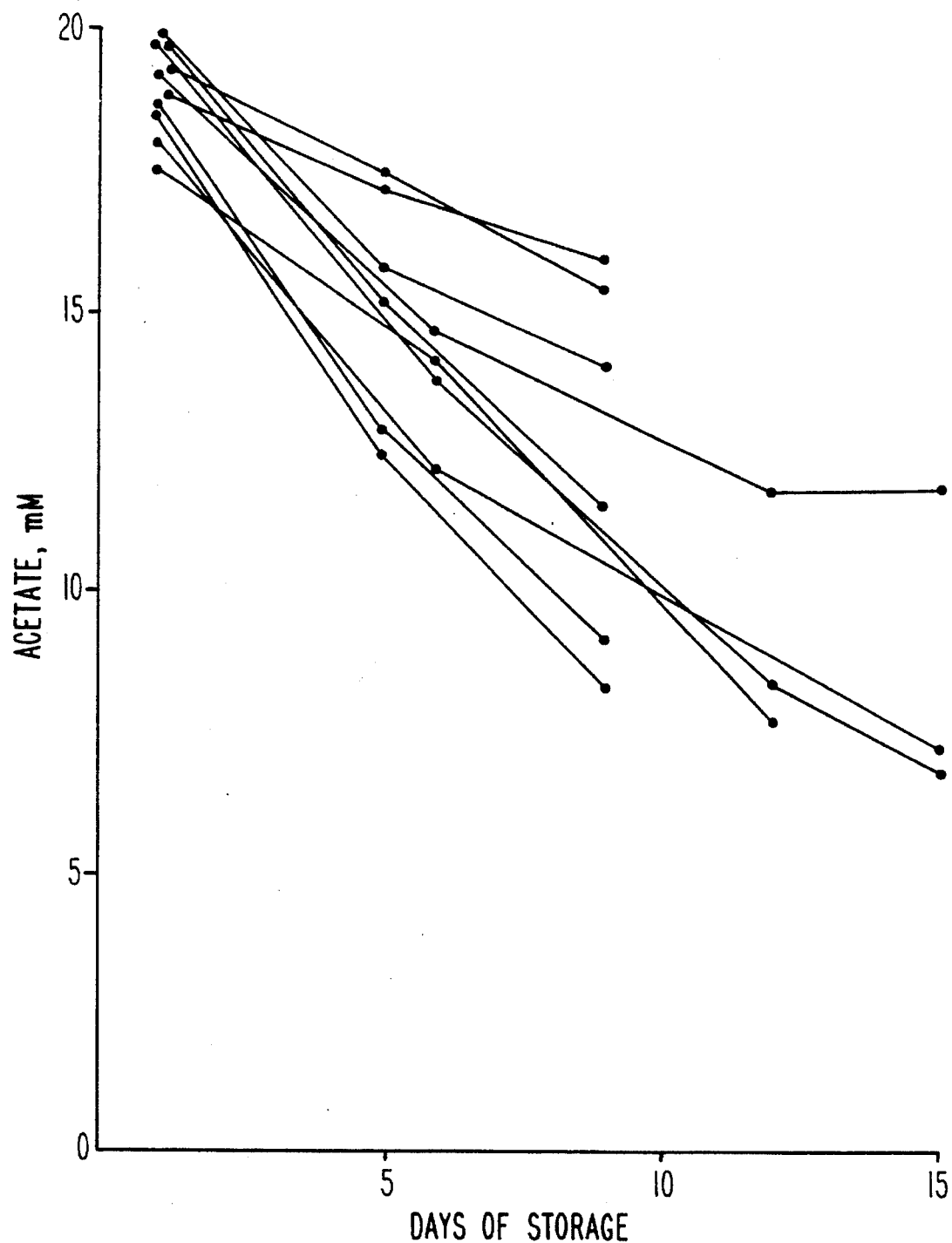
FIG. 1 is a graph showing acetate concentration (in mM) versus the days of storage.
Figure 2A:
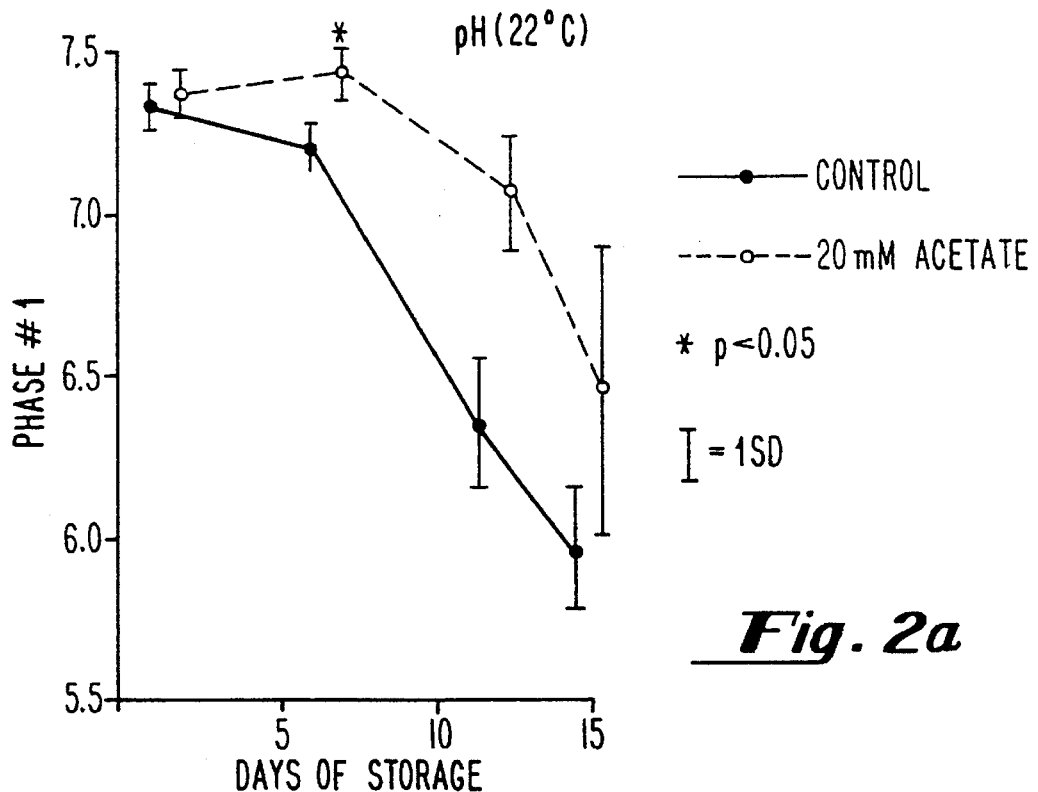
FIG. 2(a–f) shows the results of studies with pairs of PC showing changes in pH, bicarbonate, and lactate with days of storage.
Figure 2B:
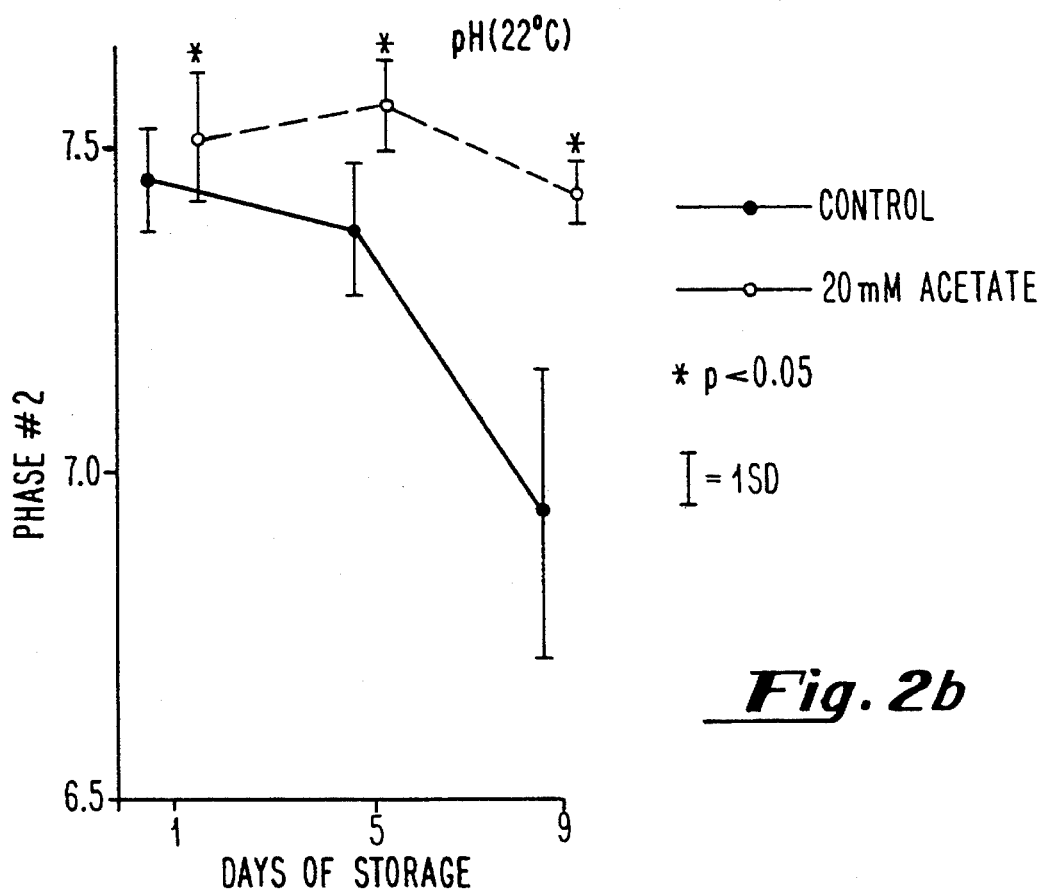
Figure 2C:
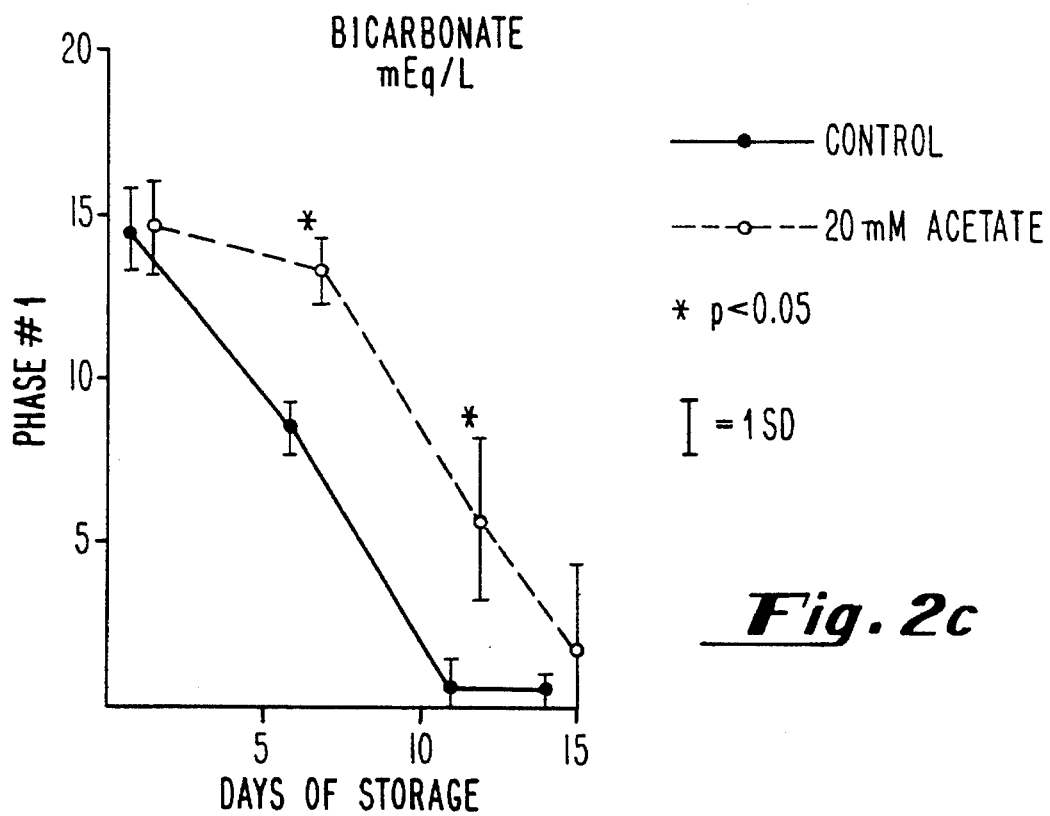
Figure 2D:
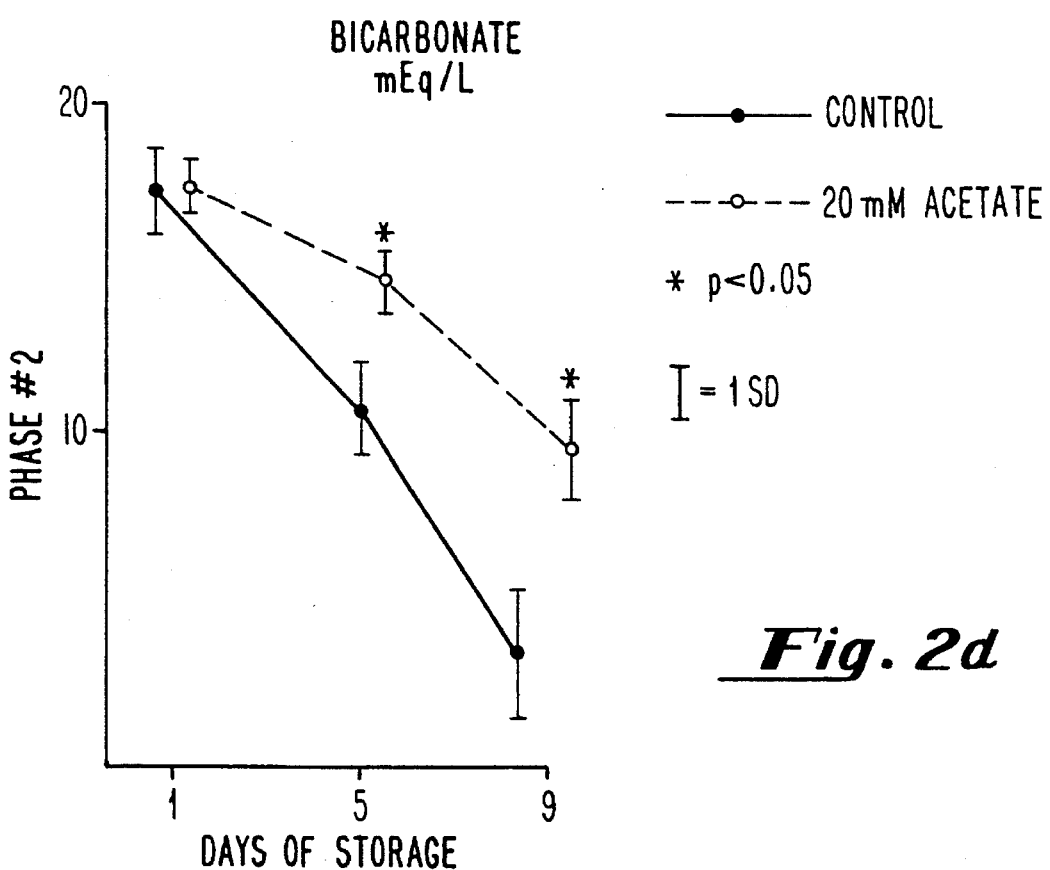
Figure 2E:
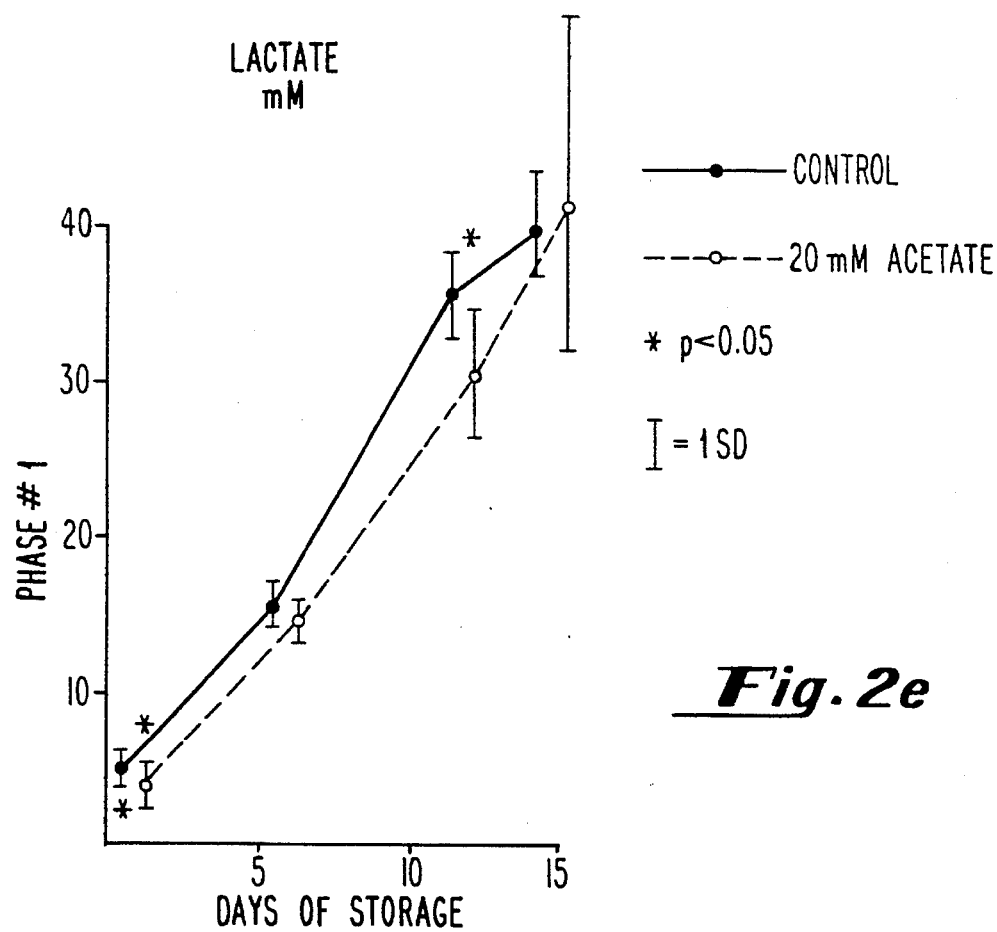
Figure 2F:
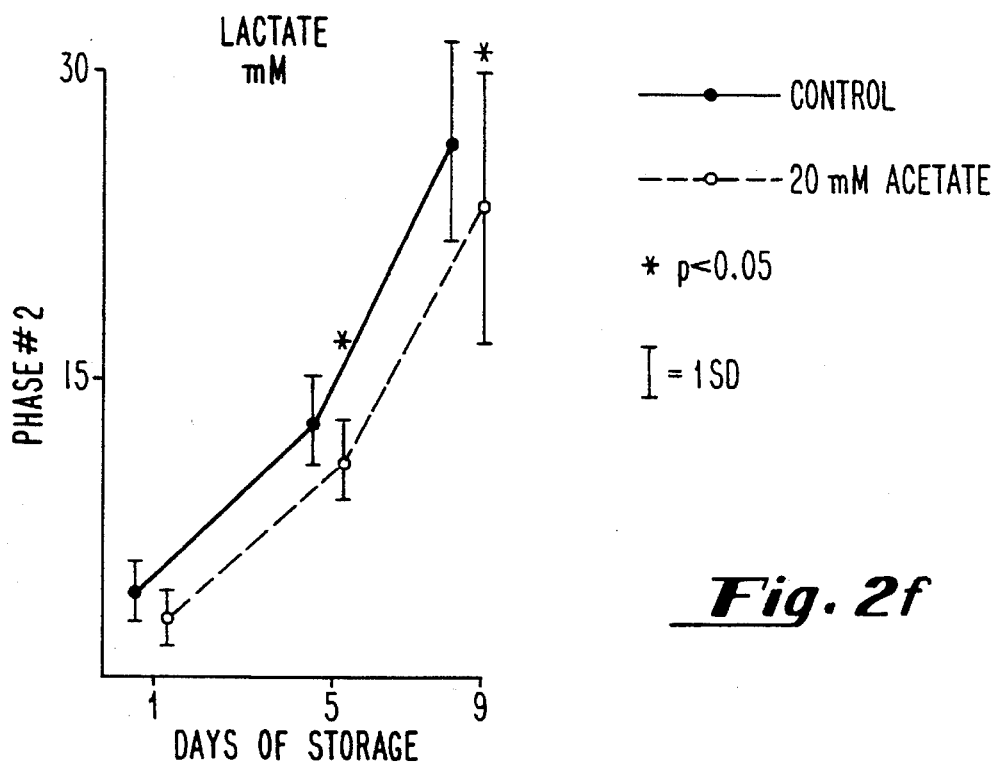

In order to maintain viability, platelets must continuously generate new adenosine triphosphate (ATP) to meet their energy needs. Two pathways are normally available: glycolysis and oxidative phosphorylation. In glycolysis, one molecule of glucose is converted to two molecules of lactic acid to generate two molecules of ATP. In oxidation, glucose, fatty acid or amino acid enters the citric acid cycle and is converted to $CO_2$ and water. This pathway requires the presence of an adequate supply of oxygen. It is much more efficient than glycolysis. Oxidative metabolism of glucose to $CO_2$ and water yields 36 molecules of ATP.

It has been recognized that platelets will meet their energy needs in a manner! which is not necessarily consistent with their long term storage in a viable condition. When given adequate oxygen, platelets produce most of their ATP through oxidation, but continue to produce lactic acid instead of diverting all metabolized glucose through the oxidative pathway. During the storage of platelets in plasma, lactic acid concentrations rise at approximately 2.5 mM per day. See Murphy et al.; "Platelet Storage at 22° C.", *Blood*, 46(2) 209–218 (1975); Murphy, "Platelet-Storage for Transfusion", Seminars in Hematology, 22(3) :165–177 (1985). This leads to gradual fall in pH. As explained in the aforementioned Murphy articles, when lactic acid reaches about 20 mM, the pH which started at 7.2 may reach 6.0. Since platelet viability is irreversibly lost if pH falls to 6.1 or below, a major limiting variable for platelet storage is pH. At this rate of lactic acid production, pH would fall much more rapidly if it were not for naturally occurring plasma buffers, principally sodium bicarbonate.

The control of the pH in the platelet concentrate storage preparation is accomplished by the present invention by the addition of a platelet storage additive to the platelets suspended in the plasma. The additives are present in the media in their solubilized state and include the compounds acetate, acetoacetate, betahydroxybutyrate, acetone, alphaketoglutarate, succinate, fumarate, malate, oxaloacetate, $C_{3-8}$ fatty acid anions such as butyrate, triose phosphates, pyruvate, and mixtures thereof. Preferred additives include acetate and pyruvate. The concentration of the additives in the platelet concentrate is up to about 40 mM, generally up to about 20 mM, preferably from about 5–20 mM, more preferably from about 10–20 mM. Although only one additive compound is necessary for proper pH Control, a mixture of additives can be used either individually in the initial concentration specified or as a combination in the initial concentration specified, however the initial concentration of all additive compounds generally does not need to exceed about 100 mM. Although not wishing to be bound to any theory of invention, it is believed that the additive agents are all organic anions and their oxidation involves their conversion to their acid form, thus allowing the removal of a hydrogen ion from the medium. The additive compounds are generally presented as acetone and salts of acetate, acetoacetate, beta-hydroxybutyrate, $C_{3-8}$ fatty acids, and pyruvic acid, such salts generally being the sodium, lithium, or potassium salts.

The amount of additive required depends upon the initial platelet count, the duration of storage, and the rate of consumption of the additive in the platelet medium. However, for a platelet count of from about 2–2.5×10$^6$ platelets/ μl preparation, the acetate consumption is about 1.5 mM/day, and thus the initial acetate level preferably is about 17–20 mM to ensure a proper pH level, above about 6.1, for a period of about 12 days. Also, for a similar platelet count, the pyruvate consumption is about 1.25 mM/day, and thus the initial pyruvate level preferably is about 15–20 mM to ensure a proper pH level for a storage period of about 12 days. Appropriate general starting levels for the other various additives can be easily determined by routine experimentation similar to that shown for acetate and pyruvate in the following Examples.

The platelet preparations are prepared by suspending the platelets in plasma. As mentioned, plasma is a known term, and when used in the context of being out of the body, includes the presence of an anticoagulant solution. Anticoagulants are known by those of skill in the art, as shown by U.S. Pat. No. 4,695,460, which is incorporated herein in its entirety. The additive, or mixture of additives, is then admixed with the plasma and platelets. The preparations are said to be "plasma-based" in that the platelets are suspended in the plasma, and anticoagulant, with the addition of a minor amount of the additive. Such a plasma-based suspension is distinct from synthetic-based media which contain synthetic, non-plasma, solutions to extend the storage of the platelets. The plasma, and anticoagulant, constitute at least about 90, preferably at least about 95, and more preferably at least about 98, percent by weight of the final platelet concentrate preparation. The platelet concentrations for storage range from about 0.8×10$^9$ to about 2.5×10$^9$ platelets/ml. Additional techniques for obtaining the platelets include platelet pheresis and the "buffy coat technique".

The invention is illustrated in the following, non-limiting examples.

EXAMPLE 1

In one embodiment of the present invention, acetate is added to optimize platelet viability during storage. To examine the effect of addition of acetate on platelets during storage in plasma, a donor underwent double plateletpheresis to obtain paired PC. For each paired study, sodium acetate was added to one of each pair in an amount calculated to achieve a concentration of 20 mM. The range of measured concentrations on day 1 of storage was 17–20 mM (n=10). The stored platelets were assessed by standard techniques such as platelet count, platelet volume, dispersion, extent of shape change, platelet aggregation, and microscopic morphology. The present invention therefore provides a composition and method which optimizes platelet viability.

In ten studies, a pair of platelet concentrates (PC) were prepared from a volunteer, normal donor using techniques previously described by Murphy (1980). 0.6 ml sodium acetate (2 mEg/L,Abbott-Labs,Chicago) was added to one of each pair. This amount was calculated to achieve a 20 mM concentration in the PC at the initiation of storage. Measured acetate concentrations were in the range of 17–20 mM, after 24 hours of storage. FIG. 1 shows that after 24 hours, the concentration of acetate fell continuously from day 1 to at least day 12 of storage. The higher rates of fall were seen in those PC with the higher concentration of platelets.

The study had two phases. In Phase 1 (4 pairs of PC), storage was carried out for 15 days with measurements made on days 1, 6, 12, and 15. In Phase 2 (6 pairs of PC), storage was carried out for 9 days with measurements made on days 1, 5, and 9. The results are shown in FIG. 2. From day 5 through day 12 of storage, pH and bicarbonate concentration were significantly higher in the PC which received acetate. The falls in pH and bicarbonate concentration were delayed by 4–5 days in the PC which received acetate, relative to the PC which did not. Thus, the addition of acetate is capable of prolonging the duration of storage by 4–5 days. FIG. 2 also shows that acetate slowed the production of lactic acid.

Detailed data from the two phases of the study are provided in Tables 1 and 2.

TABLE 1

| | PHASE 1 | | | | | | | |
|---|---|---|---|---|---|---|---|---|
| | Day 1 | | Day 6 | | Day 12 | | Day 15 | |
| | A | no A | A | no A | A | no A | A | no A |
| pH(22° C.) | 7.37 ± 0.04 | 7.31 ± 0.03* | 7.44 ± 0.04 | 7.21 ± 0.07* | 7.08 ± 0.18 | 6.33 ± 0.20* | 6.44 ± 0.47 | 5.95 ± 0.17 |
| HCO$_3$ | 14.6 ± 1.5 | 14.5 ± 1.0 | 13.3 ± 0.7 | 8.5 ± 0.4* | 5.5 ± 2.3 | 1.0 ± 0.6* | 1.8 ± 2.6 | 0.3 ± 0.1 |
| LACTATE | 4.1 ± 0.5 | 5.0 ± 0.7* | 14.3 ± 1.8 | 15.6 ± 1.1 | 30.1 ± 4.5 | 35.6 ± 2.6* | 41.2 ± 8.5 | 39.9 ± 3.6 |
| O$_2$CON | 1.25 ± 0.15 | 0.97 ± 0.25* | 0.89 ± 0.28 | 0.85 ± 0.23 | 0.60 ± 0.26 | 0.26 ± 0.23 | 0.15 ± 0.30 | 0.08 ± 0.17 |
| O$_2$CON-%1 | — | — | 70.7 ± 17.7 | 83.9 ± 12.4 | 47.3 ± 18.8 | 25.8 ± 19.3 | 12.5 ± 25.1 | 7.5 ± 14.9 |

TABLE 1-continued

| | PHASE 1 | | | | | | | |
|---|---|---|---|---|---|---|---|---|
| | Day 1 A | no A | Day 6 A | no A | Day 12 A | no A | Day 15 A | no A |
| ATP | 2.91 ± 0.19 | 2.93 ± 0.54 | 2.25 ± 0.15 | 2.31 ± 0.66 | 1.39 ± 0.53 | 0.82 ± 0.66* | 0.55 ± 0.56 | 0.14 ± 0.04 |
| ATP-%1 | — | — | 77.1 ± 0.7 | 77.6 ± 9.4 | 47.5 ± 17.2 | 26.6 ± 18.4* | 18.7 ± 19.3 | 4.6 ± 0.8 |
| Os Rev | 64.6 ± 11.2 | 62.0 ± 15.1 | 46.9 ± 7.1 | 48.2 ± 9.7 | 27.0 ± 17.4 | 14.9 ± 19.1 | 13.3 ± 14.8 | 2.1 ± 2.4 |
| Os Rev %1 | — | — | 72.9 ± 3.6 | 78.5 ± 5.5 | 39.5 ± 19.9 | 20.9 ± 25.9 | 18.5 ± 18.9 | 3.2 ± 3.6 |
| % Discs | 82.5 ± 9.6 | 85.0 ± 10.0 | 62.5 ± 35.9 | 60.0 ± 38.3 | 32.5 ± 39.8 | 10.0 ± 14.1* | 16.3 ± 29.3 | 0.0 ± 0.0 |
| PLCT %1 | — | — | 95.1 ± 3.9 | 87.8 ± 8.8 | 83.2 ± 6.2 | 78.1 ± 13.6 | 74.1 ± 4.6 | 76.3 ± 13.3 |
| DISP | 1.72 ± 0.11 | 1.79 ± 0.18 | 1.79 ± 0.07 | 1.82 ± 0.15 | 1.91 ± 0.14 | 1.98 ± 0.19 | 2.16 ± 0.25 | 2.24 ± 0.22 |
| MPV %1 | — | — | 98 ± 4 | 104 ± 6* | 104 ± 4 | 139 ± 13* | 152 ± 43 | 164 ± 20 | data presented as means ± 1 SD
*p < 0.05, paired t-test
n = 4

TABLE 2

| | PHASE 2 | | | | | |
|---|---|---|---|---|---|---|
| | Day 1 A | no A | Day 5 A | no A | Day 9 A | no A |
| pH(22° C.) | 7.51 ± 0.10 | 7.45 ± 0.08* | 7.56 ± 0.10 | 7.38 ± 0.10 | 7.43 ± 0.06 | 6.94 ± .21* |
| $HCO_3$ | 17.9 ± 0.84 | 17.8 ± 1.3 | 14.6 ± 1.0 | 10.7 ± 1.3* | 9.5 ± 1.6 | 3.4 ± 1.4* |
| LACTATE | 3.6 ± 1.2 | 4.3 ± 0.9 | 11.3 ± 2.2 | 13.1 ± 2.1* | 22.0 ± 5.9 | 25.0 ± 4.6* |
| $O_2$CON | 1.55 ± 0.22 | 1.36 ± 0.23 | 1.33 ± 0.19 | 1.04 ± 0.15 | 1.04 ± 0.21 | 0.92 ± 0.22 |
| $O_2$CON %1 | — | — | 85.9 ± 8.0 | 77.3 ± 3.7* | 66.5 ± 7.6 | 67.8 ± 13.22 |
| ATP | 3.32 ± 0.48 | 4.12 ± 0.56 | 3.26 ± 0.70 | 3.15 ± 0.26 | 2.47 ± 0.79 | 2.32 ± 0.51 |
| ATP %1 | — | — | 98.1 ± 11.1 | 77.7 ± 13.1 | 74.9 ± 23.8 | 56.7 ± 11.7 |
| Os Rev | 66.8 ± 13.4 | 66.1 ± 9.8 | 46.6 ± 2.9 | 53.5 ± 7.9* | 39.0 ± 4.4 | 40.6 ± 8.3 |
| Os Rev %1 | — | — | 71.5 ± 11.3 | 81.4 ± 10.7 | 59.9 ± 11.3 | 61.4 ± 9.1 |
| % Discs | 88.3 ± 2.6 | 80.0 ± 16.7 | 60.8 ± 24.6 | 66.7 ± 21.6 | 43.3 ± 31.4 | 39.2 ± 28.7 |
| PLCT %1 | — | — | 96.2 ± 2.1 | 94.1 ± 2.4* | 87.4 ± 3.6 | 88.3 ± 6.8 |
| DISP | 1.67 ± 0.1 | 1.67 ± .03 | 1.68 ± .03 | 1.66 ± .02* | 1.71 ± .03 | 1.68 ± .01 |
| MPV %1 | — | — | 104 ± 5 | 103 ± 4 | 107 ± 5 | 115 ± 11 | data presented as means ± 1 SD
p < 0.05, paired t-test
n = 6

The rate of oxygen consumption (02CON) is greater in the PC with acetate, indicating that a fuel for oxidative metabolism has been added. The other measurements, ATP, osmotic reversal reaction (Os Rev), % discs by phase microscopy (% discs), platelet count (PLCT) and mean platelet volume (MPV) as percentage of day 1 value, and dispersion (DISP) of the platelet size distribution, all reflect platelet quality. On day 12 (Phase 1), ATP, discs, and maintenance of MPV are all superior in the PC which received acetate, reflecting the superior maintenance of pH when acetate is added to the platelet preparation.

EXAMPLE 2

Figure 3A:
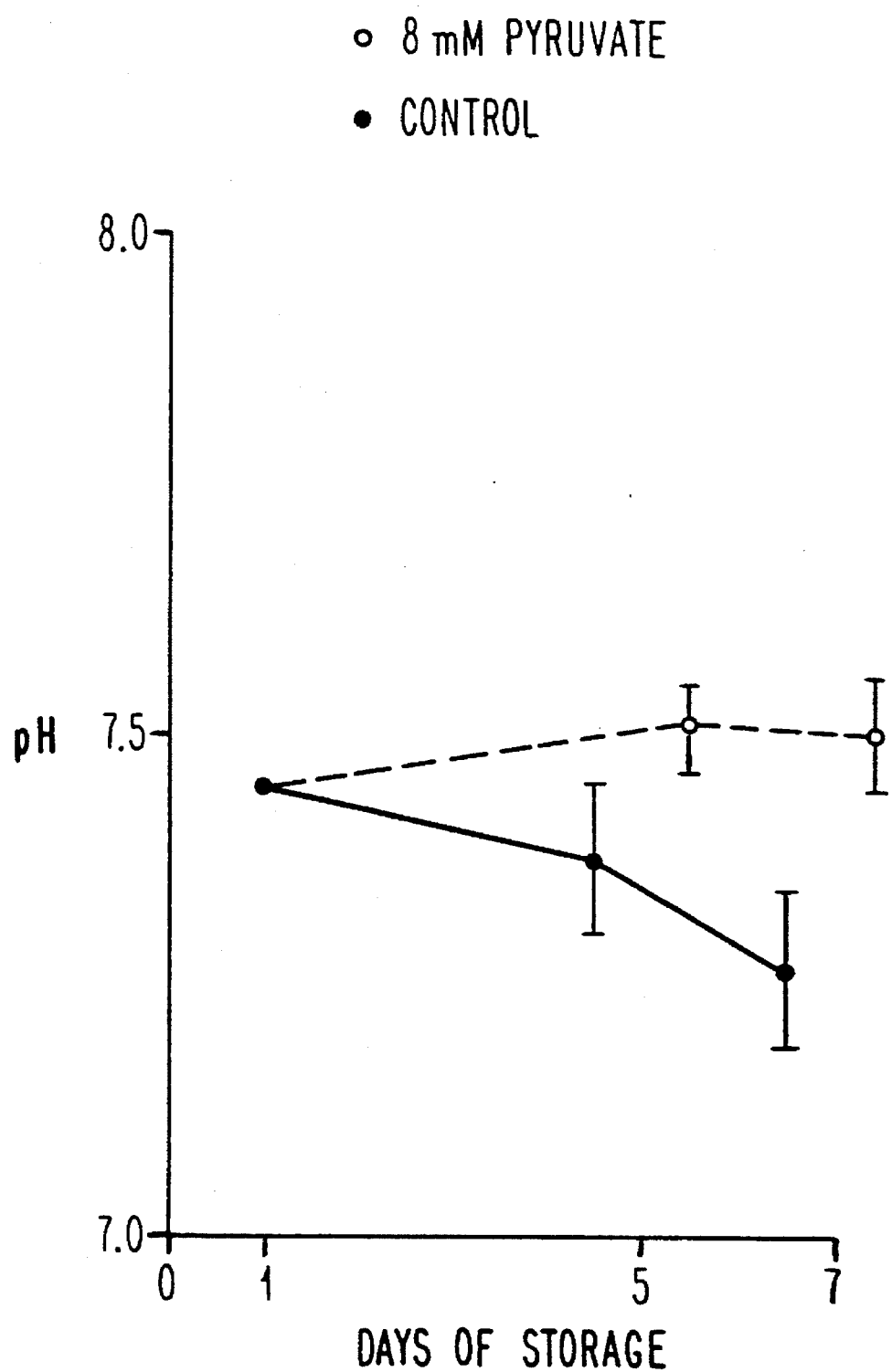
FIG. 3(a–c) shows the results of studies with platelet concentrates showing changes in pH, bicarbonate levels, and lactate levels with days of storage.
Figure 3B:
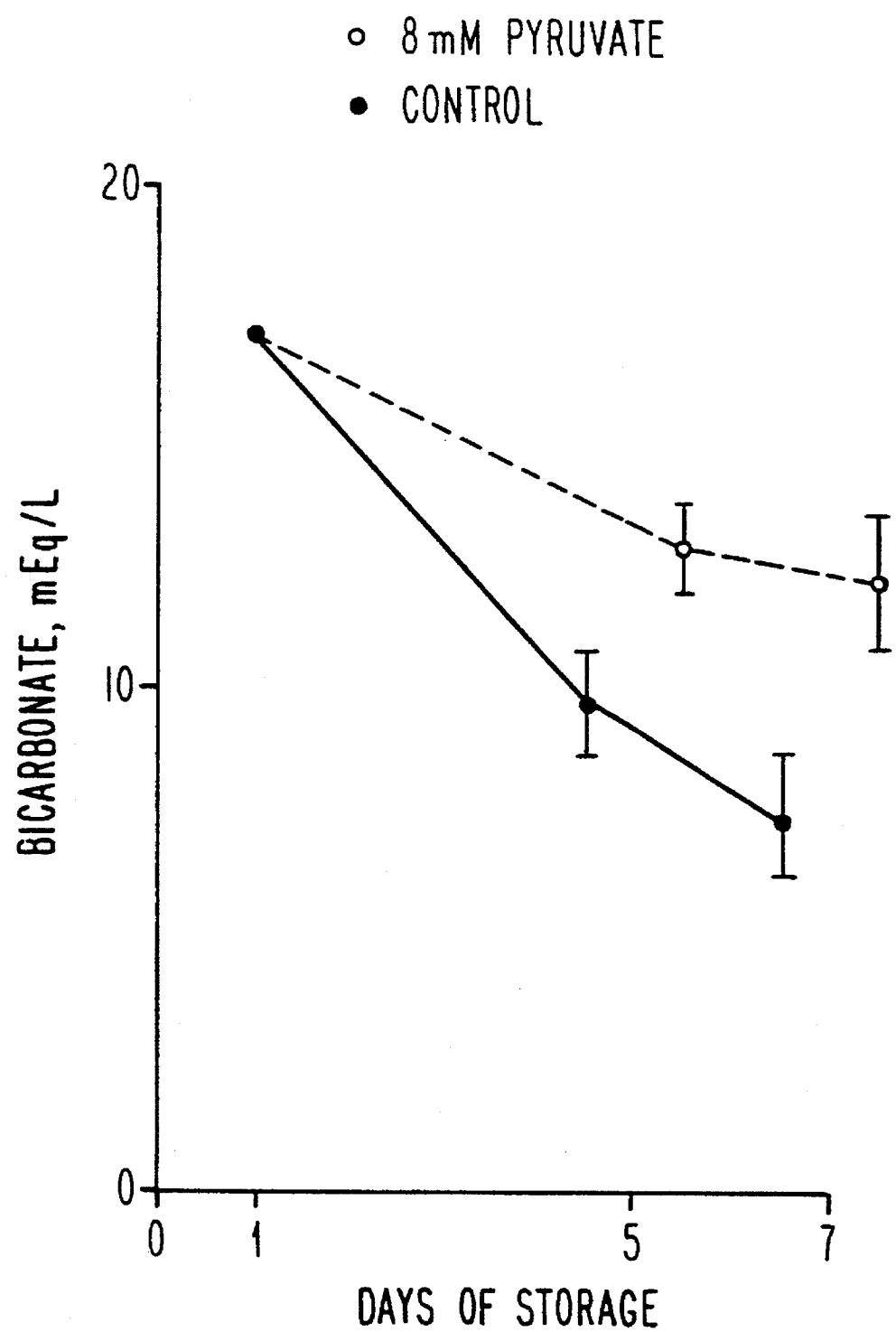
Figure 3C:
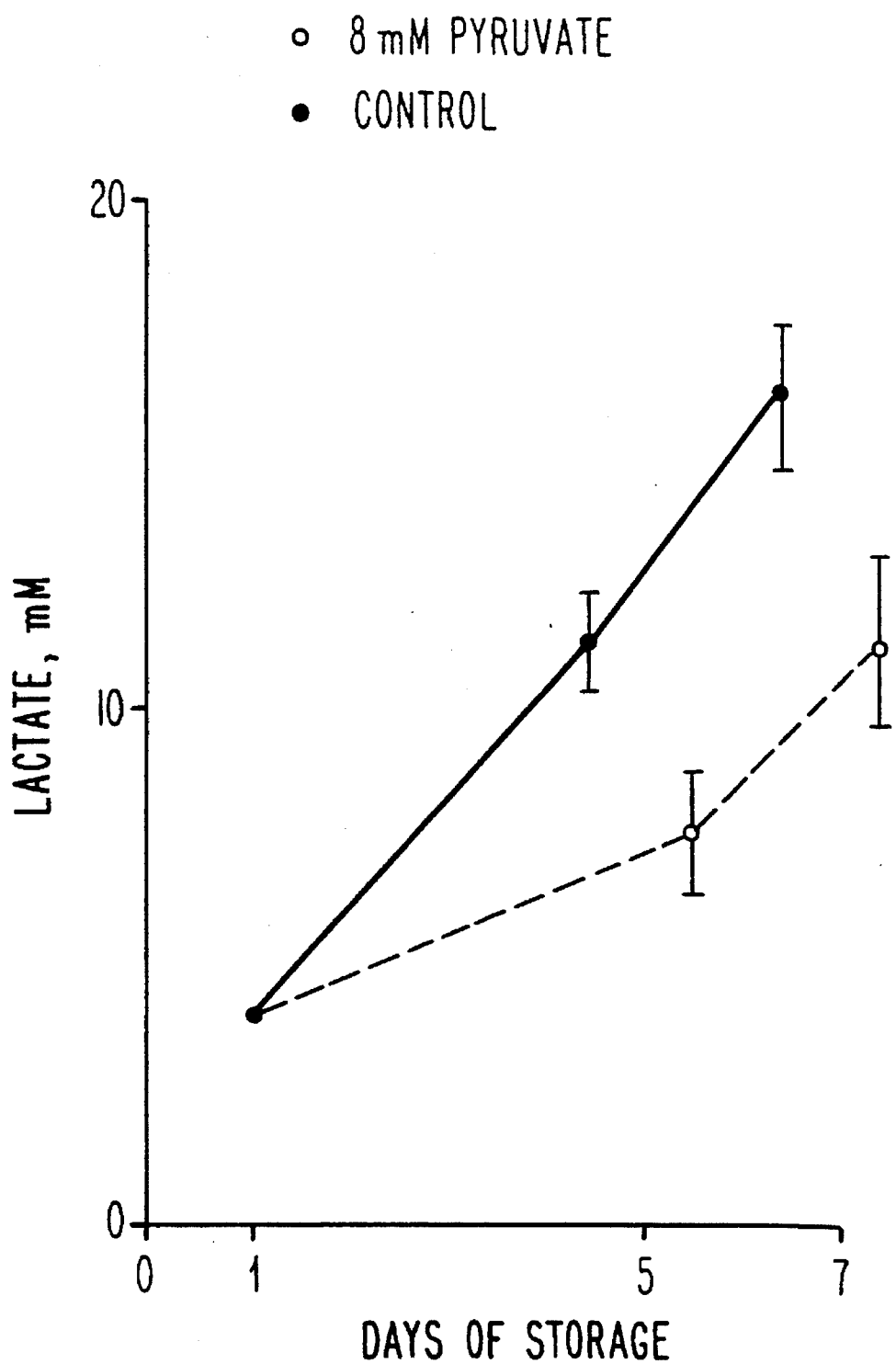

Platelet concentrate preparations were prepared using the procedures of Example 1, but replacing the acetate with pyruvate. The pyruvate was added in an amount to provide an initial pyruvate concentration of about 8 mM. The results of the storage of the pyruvate preparations compared to the control preparation, with no additives, are shown in FIGS. 3(a)–(c). In FIG. 3(a) it is shown that the pH was maintained for a period of seven (7) days while the control pH dropped during that period. In FIG. 3(b) it is shown that the bicarbonate level decreased at a lesser rate than in the control. In FIG. 3(c), it is shown that the lactate production is decreased by the presence of the pyruvate. The data for days 5 and 7 are set forth in Table 3.

TABLE 3

| | pH | | Bicarbonate Level (m Eq/L) | | Lactate Level (mM) | |
|---|---|---|---|---|---|---|
| Preparation | Day 5 | Day 7 | Day 5 | Day 7 | Day 5 | Day 7 |
| Control | 7.38 ± .07 | 7.29 ± .08 | 9.8 ± 0.5 | 7.4 ± 0.7 | 11.4 ± 0.9 | 16.1 ± 1.1 |
| Pyruvate | 7.51 ± .04 | 7.51 ± .05 | 12.8 ± 0.4 | 12.1 ± 1.2 | 7.4 ± 1.1 | 11.2 ± 1.4 |

EXAMPLE 3

Figure 4:
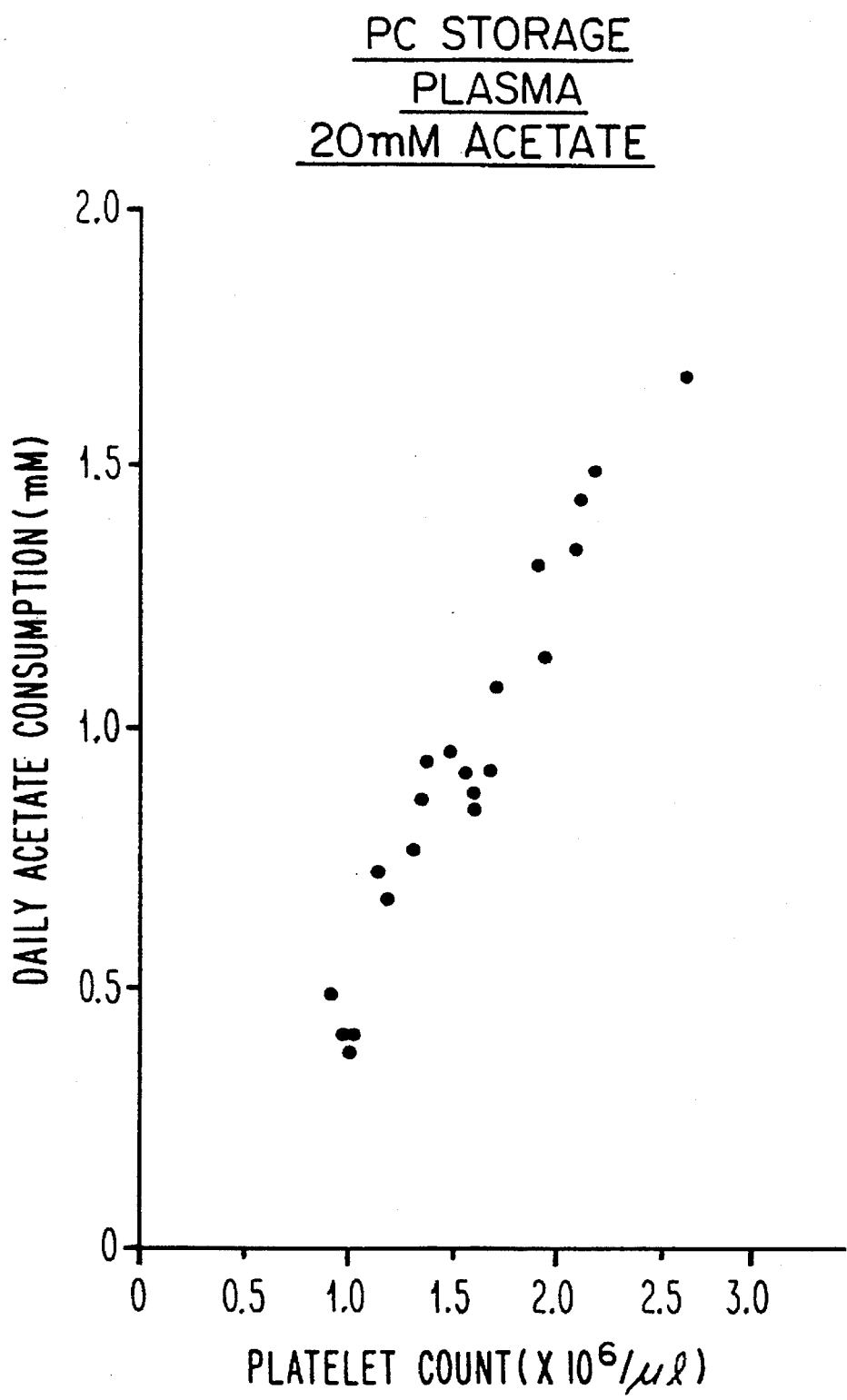
FIG. 4 shows the daily acetate consumption by various platelet concentrates containing varying platelet concentrations.
Figure 5:
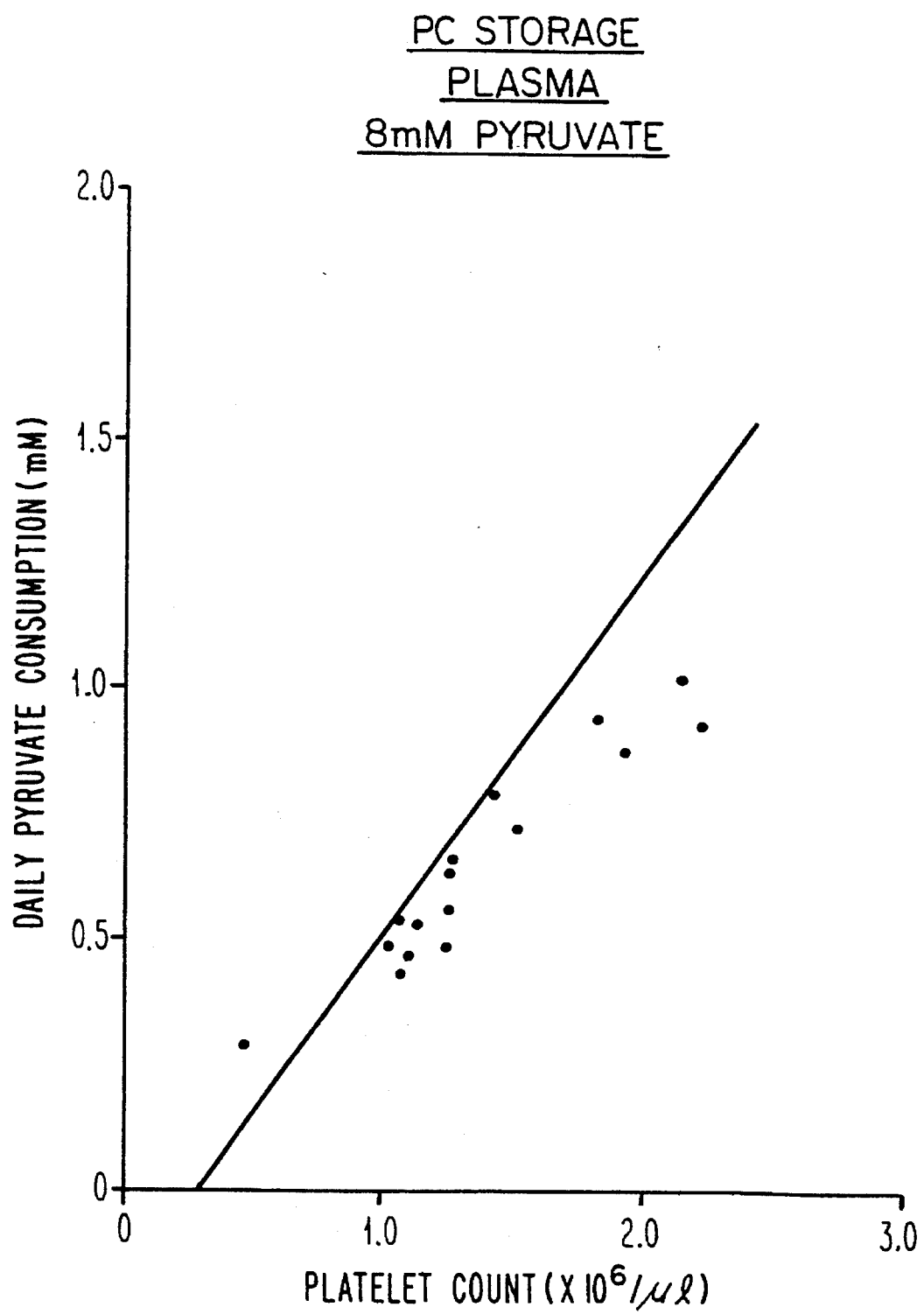
FIG. 5 shows the daily pyruvate consumption by various platelet concentrates containing varying platelet concentrations.

The daily acetate and pyruvate consumption was determined as a function of platelet concentration in the platelet concentrates. Platelet concentrate preparations were prepared according to Example 1 for the acetate additive preparations and according to Example 2 for the pyruvate additive preparations. The initial acetate concentration was 20 mM and the initial pyruvate concentration was 8 mM. The results are set forth in FIGS. 4 and 5 for the acetate and pyruvate preparations, respectively.

EXAMPLE 4

Platelet concentrate preparations were prepared using the procedures of Example 1, but replacing the acetate with additive compounds acetoacetate, in the form of acetoacetic acid, or beta-hydroxybutyrate, in the form of D,L-3-betahydroxybutyrate. The additive compounds were added in an amount to provide an initial acetoacetate concentration of about 15 mM or an initial beta-hydroxybutyrate concentration of about 30 mM.

Six pairs of platelet concentrates (PC) (one of each pair being the control) were prepared for the acetoacetate (AA) study, and five pairs of PC were prepared for the betahydroxybutyrate (HB) study. The pH maintenance and bicarbonate consumption were monitored during the storage period. Data was collected on days 1, 5, 7, and 10 of the study, however data for three of the six AA PC pairs was not obtained on day 10.

Figure 6:
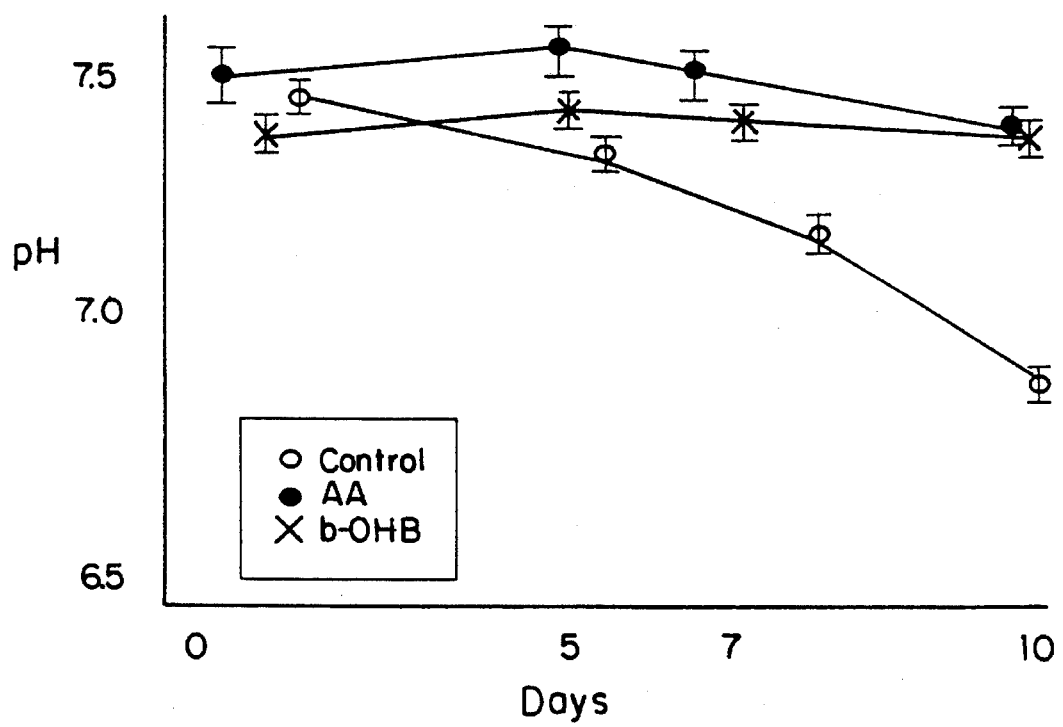
FIG. 6 shows the results of studies with platelet concentrates showing changes in pH over time for the additive compounds acetoacetate and beta-hydroxybutyrate.

The control of the PC pH by the additive compounds is shown in FIG. 6. The pH of the AA and BH (denoted as b-OHB) PC was maintained throughout the ten day experimentation period, whereas the control PC pH dropped significantly.

The rates of utilization of bicarbonate (mEq/liter/day) were calculated for each PC using linear regression analysis. The results are shown in Table 4.

TABLE 4

| PC | Bicarbonate Utilization Rate (mEq/L/day) | pValue |
|---|---|---|
| Acetoacetate (AA) | 1.28 ± 0.4 | 0.154 |
| Control - AA | 1.56 ± 0.4 | |
| beta-hydroxybutyrate (HB) | 1.08 ± 0.2 | 0.001 |
| Control - HB | 1.58 ± 0.2 | |

Because the p value for the AA study compared to the control was only 0.154, a paired t test was performed comparing the actual bicarbonate values (mEq/liter) on days 5, 7, and 10, the results are shown in Table 5 for both the AA and the BH study.

TABLE 5

| | Daily Bicarbonate Values (mEq/L) | | | | | |
|---|---|---|---|---|---|---|
| DAY | AA | CONTROL | p VALUE | HB | CONTROL | p VALUE |
| 5 | 17.4 ± 1.9 | 10.7 ± 1.4 | 0.001 | 12.4 ± 1.4 | 10.7 ± 1.5 | 0.02 |
| 7 | 13.4 ± 1.7 | 7.6 ± 0.9 | 0.006 | 10.4 ± 1.3 | 7.6 ± 1.4 | 0.006 |
| 10 | 7.1 ± 1.1 | 2.8 ± 1.2 | 0.084 | 6.8 ± 1.2 | 2.9 ± 1.2 | 0.000 |

The borderline statistical significance on day 10 for AA is clearly due to the fact that only three PC pairs were assayed.

What is claimed is:

1. A human blood, plasma-based platelet concentrate preparation for the storage of platelets, consisting essentially of:

(a) platelets;

(b) plasma and anticoagulant, wherein said plasma and anticoagulant are present in an amount of at least 90 percent by weight of the concentration preparation and wherein said platelets are dispersed in said plasma and anticoagulant; and (c) an additive for extending the storage of the platelets selected from the group consisting of acetoacetate, betahydroxybutyrate, acetone, alpha-ketoglutarate, oxaloacetate, $C_{3-8}$ fatty acid anions, triose phosphates, pyruvate, and mixtures thereof, wherein said additive is present in an amount of from about 5 to 100 mM, wherein the pH of said preparation is at least 6.1.

2. The preparation of claim 1 wherein said additive is present in an amount of up to about 40 mM.

3. The preparation of claim 1 wherein said additive is present in an amount of up to about 20 mM.

4. The preparation of claim 3 wherein the additive comprises pyruvate.

5. The preparation of claim 4 wherein the pyruvate is present in an amount of from about 5–20 mM.

6. The preparation of claim 4 wherein the plasma and anticoagulant constitute at least about 95 percent by weight of the preparation.

7. A human blood, plasma-based platelet concentrate preparation for the storage of platelets, consisting essentially of:

(a) platelets;

(b) plasma and anticoagulant, wherein said plasma and anticoagulant are present in an amount of at least 95 percent by weight of the concentration preparation and wherein said platelets are dispersed in said plasma and anticoagulant; and (c) an additive for extending the storage of the platelets selected from the group consisting of acetoacetate, betahydroxybutyrate, acetone, alpha-ketoglutarate, oxaloacetate, $C_{3-8}$ fatty acid anions, triose phosphates, pyruvate, and mixtures thereof, wherein said additive is present in an amount of from about 5 to 100 mM, wherein the pH of said preparation is at least 6.1.

8. The preparation of claim 7 wherein said additive is present in an amount of up to about 40 mM.

9. The preparation of claim 8 wherein said plasma and anticoagulant constitute at least about 98 percent by weight of the preparation.

10. The preparation of claim 9 wherein said additive is present in an amount of up to about 20 mM.

11. The preparation of claim 9 wherein the additive comprises pyruvate.

12. The preparation of claim 10 wherein the additive comprises pyruvate.

13. A method of storing a human blood platelet preparation, consisting essentially of:

(a) providing a human blood, plasma-based platelet concentrate consisting essentially of:

(1) platelets;

(2) plasma and anticoagulant, wherein said plasma and anticoagulant are present in an amount of at least 90 percent by weight of the concentration preparation and wherein said platelets are dispersed in said plasma and anticoagulant; and (3) an additive for extending the storage of the platelets selected from the group consisting of acetoacetate, beta-hydroxybutyrate, acetone, alpha-ketoglutarate, succinate, fumarate, malate, oxaloacetate, $C_{3-8}$ fatty acid anions, triose phosphates, pyruvate, and mixtures thereof, wherein said additive is present in an amount of from about 5 to 100 mM; and (b) storing the concentrate for an extended period of time of at least 5 days while maintaining the pH at a level of at least pH 6.1.

14. The method of claim 13 wherein said additive is added in an amount of up to about 40 mM.

15. The method of claim 13 wherein said additive is added in an amount of from about 5–20 mM.

16. The method of claim 15 wherein said additive comprises pyruvate.

17. The method of claim 16 wherein the amount of added pyruvate is from about 5–20 mM.

18. The method of claim 13 wherein the plasma and anticoagulant constitute at least about 95 percent by weight of the preparation.

19. The method of claim 13 wherein the plasma and anticoagulant constitute at least about 98 percent by weight of the preparation.

20. A human blood, plasma-based platelet concentrate preparation for the storage of platelets, consisting essentially of:

(a) platelets;

(b) plasma and anticoagulant, wherein said plasma and anticoagulant are present in an amount of at least 95 percent by weight of the concentration preparation and wherein said platelets are dispersed in said plasma and anticoagulant; and (c) an additive for extending the storage of the platelets selected from the .group consisting of fumarate and malate, and mixtures thereof, wherein said additive is present in an amount of from about 10 to 40 mM.

* * * * *